United States Patent
Becher et al.

(10) Patent No.: US 8,728,611 B2
(45) Date of Patent: May 20, 2014

(54) STENT

(75) Inventors: Baerbel Becher, Rostock (DE); Carsten Momma, Rostock (DE)

(73) Assignee: BIOTRONIK SE & Co. KG, Berlin (DE)

( * ) Notice: Subject to any disclaimer, the term of this patent is extended or adjusted under 35 U.S.C. 154(b) by 870 days.

(21) Appl. No.: 10/552,593

(22) PCT Filed: Apr. 5, 2004

(86) PCT No.: PCT/EP2004/003630
§ 371 (c)(1),
(2), (4) Date: Nov. 10, 2006

(87) PCT Pub. No.: WO2004/089247
PCT Pub. Date: Oct. 21, 2004

(65) Prior Publication Data
US 2007/0168015 A1   Jul. 19, 2007

(30) Foreign Application Priority Data
Apr. 10, 2003   (DE) .................................. 103 17 241

(51) Int. Cl.
*A61F 2/06*   (2013.01)
(52) U.S. Cl.
USPC ....... 428/195.1; 623/1.19; 623/1.2; 623/1.34; 623/1.44
(58) Field of Classification Search
USPC ................................ 428/195.1; 623/1.1–1.46
See application file for complete search history.

(56) References Cited

U.S. PATENT DOCUMENTS

| | | | |
|---|---|---|---|
| 5,800,511 A * | 9/1998 | Mayer | 623/1.34 |
| 5,919,126 A | 7/1999 | Armini | |
| 6,077,880 A | 6/2000 | Castillo et al. | |
| 6,193,752 B1 | 2/2001 | Hildebrant | |
| 6,241,691 B1 | 6/2001 | Ferrera et al. | |
| 6,312,456 B1 | 11/2001 | Kranz et al. | |
| 6,398,806 B1 | 6/2002 | You | |
| 6,471,721 B1 | 10/2002 | Dang | |
| 2001/0001317 A1 | 5/2001 | Duerig et al. | |

FOREIGN PATENT DOCUMENTS

| | | |
|---|---|---|
| DE | 196 53 720 A1 | 6/1998 |
| DE | 197 29 279 A1 | 1/1999 |
| DE | 100 64 596 A1 | 6/2002 |
| EP | 0 824 900 A2 | 2/1998 |
| EP | 1 290 984 A2 | 3/2003 |
| WO | WO 99/02195 | 1/1999 |
| WO | WO 99/65623 | 12/1999 |
| WO | WO 00/10469 | 3/2000 |
| WO | WO 01/45578 A2 | 6/2001 |
| WO | WO 01/49340 A1 | 7/2001 |
| WO | WO 02/24111 A2 | 3/2002 |
| WO | WO 02/26281 A1 | 4/2002 |
| WO | WO 02/39927 A2 | 5/2002 |
| WO | WO 02/40077 A2 | 5/2002 |

* cited by examiner

Primary Examiner — Gerard Higgins
(74) Attorney, Agent, or Firm — Greer, Burns & Crain, Ltd.

(57) ABSTRACT

A stent comprises a metallic, relatively radiolucent carrier structure and at least one marker element which includes comparatively radiopaque material. The radiopaque material is completely enclosed by a cover layer of a material other than the radiopaque material, the cover layer including metal or a metal compound. The stent may be used to treat a patient.

13 Claims, 4 Drawing Sheets

STENT

BACKGROUND OF THE INVENTION

The invention concerns a stent having a metallic, relatively radiolucent carrier structure and at least one marker element comprising comparatively radiopaque material.

Stents are endovascular prostheses which serve inter alia for the treatment of stenoses, that is to say, vessel constrictions. Stents usually have a tubular carrier structure which is open at both longitudinal ends of the tube and which is formed by legs and openings enclosed by the legs. Stents of that kind can usually assume two conditions, more specifically a compressed condition of a small diameter and an expanded condition of a comparatively larger diameter. In the compressed condition, such a stent can be introduced by means of a catheter into for example a blood vessel and can be positioned at a location to be treated. The stent is expanded or is allowed to expand of its own accord, at the treatment location. Stents which are not self-expanding are usually expanded by means of an inflatable balloon at a distal end of a catheter for insertion of the stent. Stents of that kind are therefore referred to as balloon-expanded. Other stents have the property of expanding of their own accord, for example by virtue of inherent spring forces. Stents of that kind are referred to as self-expanding. The self-expanding stents include in particular those which have a carrier structure comprising a shape memory metal such as nitinol, a known titanium nickel compound. Shape memory metals of that kind have the property of retaining a first shape or being plastically deformable below a given change temperature, and assuming a second shape when the change temperature is exceeded. In regard to stents, shape memory metals are used in such a way that the first shape corresponds to the compressed condition of a stent and the second shape corresponds to the expanded condition of a stent.

In the expanded condition of a stent, it serves, for example, for the treatment of vessel constrictions (stenoses), acting as a vessel support which keeps a blood vessel to be treated open at a constricted location. The expanded stent acts in opposition to the vessel constriction and supports the vessel wall in the region of the vessel constriction. For that purpose, the stent must enjoy adequate radial strength or carrying force. The carrier structure of the stent must also afford adequate surface coverage in order adequately to support the vessel constriction. On the other hand, the requirement for being able to expand the stent means that openings are necessarily present between the legs of the carrier structure of a stent. In the compressed condition of the stent, those openings can be substantially closed. In the expanded condition of the stent, the opening is enlarged in any case.

Besides an adequate carrying force, stents must also involve adequate flexibility with respect to their longitudinal axis in order to be able to follow movements of the vessel. In addition there is a wish for longitudinal changes in a stent upon expansion to be kept as small as possible. Finally the material of the stent or at least the surface thereof should be as body-compatible as possible.

Those requirements have resulted in various, very sophisticated and diversified stent configurations. The stents which are of interest here have a carrier structure produced from a metal tube as the starting material. Cutting the metal tube for example by means of a laser or spark erosion produces the legs, as remaining material. Cut legs of that kind have the great advantage over stents of the first generation, which were shaped from wire, that the geometry of the carrier structure can be optimized in regard to the various different demands involved.

That large number of demands made on stents further includes the requirement that the stent is to be capable of being positioned with the utmost accuracy. In general, the operation of positioning a stent is effected by means of imaging processes which, for example, operate with X-rays. In this connection, there is generally the disadvantage that materials which are suitable for the carrier structure of a stent frequently can only be detected with difficulty by means of the imaging processes used as the material forming the carrier structure is relatively radiolucent. It is therefore known to provide stents with what are referred to as X-ray markers containing a relatively radiopaque material which is easy to locate by means of the above-specified imaging processes. A known radiopaque material is for example, gold.

Usually, the need to provide X-ray markers in stents of the above-described kind forces compromises in terms of the stent design, which are possibly detrimental to others of the above-mentioned desired properties.

An aspect of the present invention is to provide a stent which is X-ray visible and which moreover combines together as many as possible of the desirable properties.

BRIEF SUMMARY OF THE INVENTION

In accordance with the invention, that object is attained by a stent of the kind set forth in the opening part of this specification, wherein after the cutting-out operation, the marker element (22) is welded to the rest of the carrier structure (12, 16) and the radiopaque material is completely enclosed by a cover layer of a material other than the radiopaque material, the cover layer including metal or a metal compound.

The invention is based on the basic idea of integrating radiopaque material as an X-ray marker for a stent into the carrier structure of the stent in such a way that the outwardly acting surface of the stent in the region of the X-ray marker is not characterized by the radiopaque material but by another metal or a metal compound. The metal of the cover layer of the marker element advantageously makes it possible for the marker element to be welded to the rest of the carrier structure after it has been cut out. The outwardly acting surface of the X-ray marker in that case can be for example of a body-compatible nature by virtue of a silicon carbide coating. In a particularly advantageous variant, the metal forming the cover layer is identical to the metal of the carrier structure and can therefore be easily connected to the rest of the carrier structure by welding without contact corrosion or the like occurring.

The last-mentioned property is particularly advantageous in connection with a stent having a self-expanding carrier structure, for example, comprising a shape memory metal such as nitinol. In that case, it is possible for the X-ray marker to be provided in the form of a hollow nitinol wire which is filled in the interior with gold and which is to be easily welded to the rest of the carrier structure of the stent. In that way the X-ray marker can even be integrated into the carrier structure.

In preferred variants, a stent of that kind, in particular a self-expanding nitinol stent of that kind, is drug-coated. Suitable drugs contain active substances with inflammation-inhibiting and proliferation-inhibiting effect. Such active substances are for example Sartane or cyclospurin A which are joined to the carrier structure of the stent by means of a polymer carrier matrix. After implantation of the stent, the active substance or substances can elute into the body tissue and deploy their desired inflammation-inhibiting or proliferation-inhibiting effect. The active substances can thus contribute to avoiding unwanted re-stenosis or unwanted inflammation.

BRIEF DESCRIPTION OF THE SEVERAL VIEWS OF THE DRAWINGS

The invention will now be described by means of embodiments by way of example with reference to the accompanying Figures in which.

DETAILED DESCRIPTION OF THE INVENTION

Figure 1:
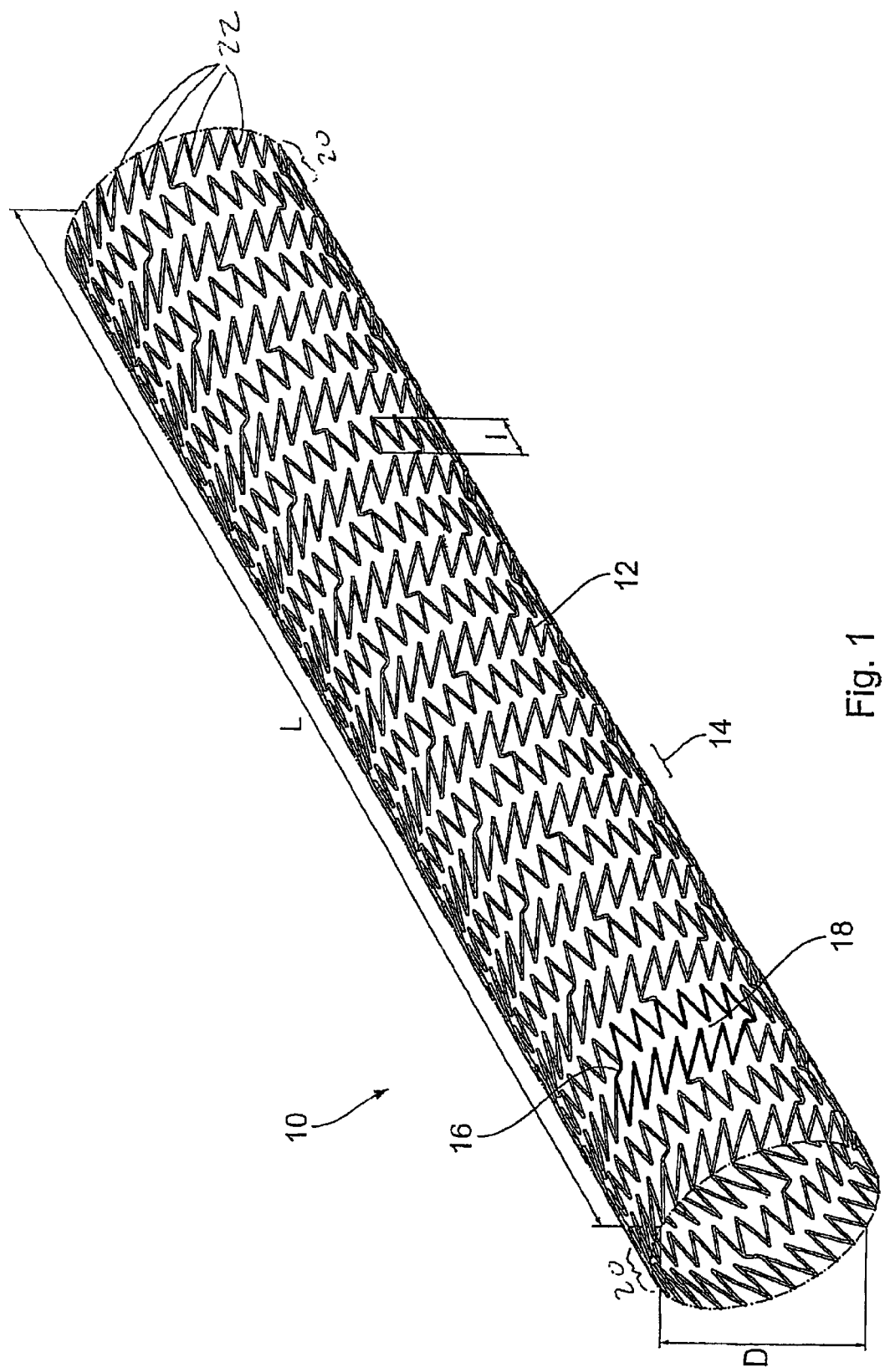
FIG. 1 is a diagrammatic view of a stent.
Figure 2:
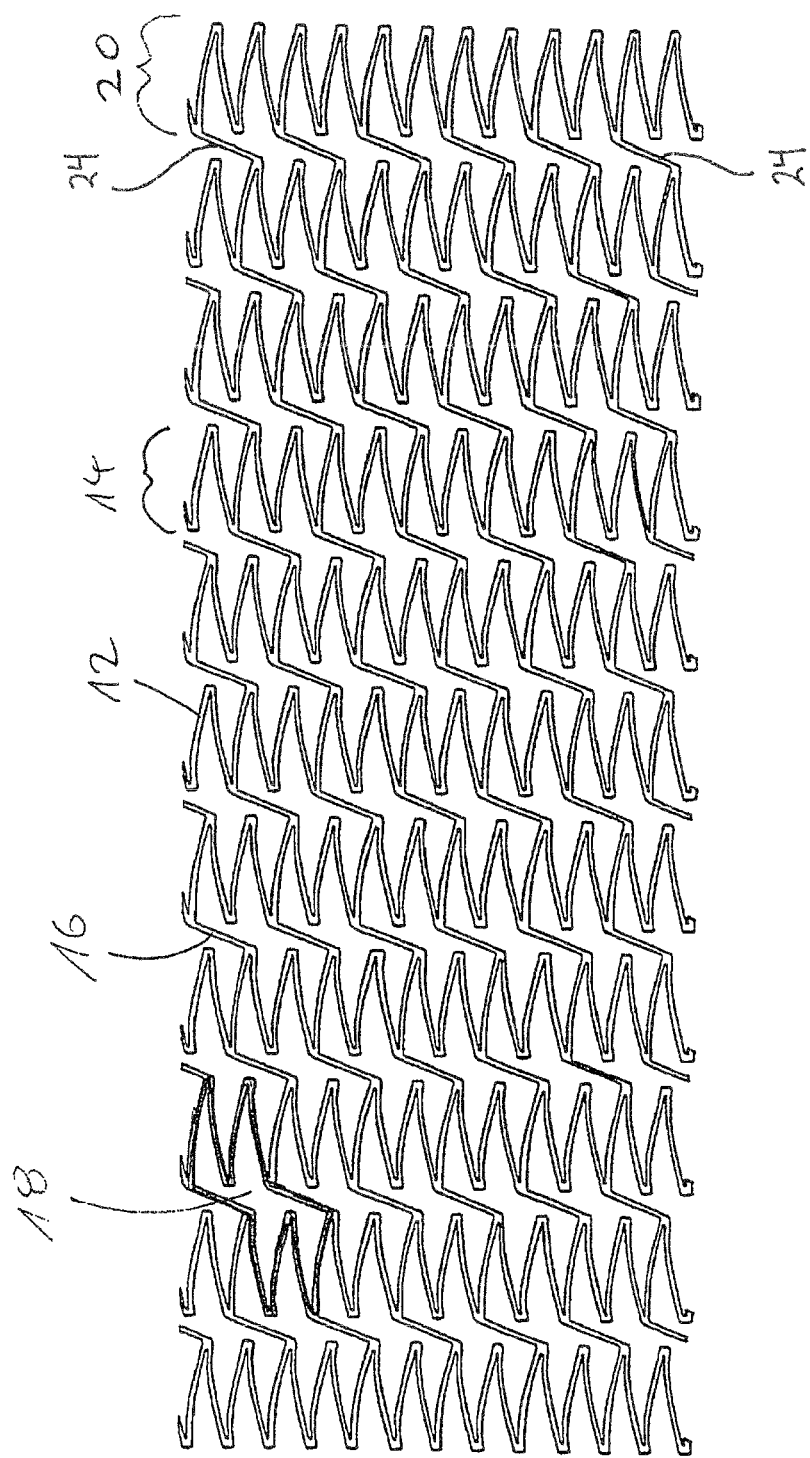
FIG. 2 shows an example of a development of the carrier structure of a stent, which forms a stent peripheral wall.

The stent 10 shown in FIG. 1 is in the form of a hollow body which is open at its ends and the peripheral wall of which is formed by a carrier structure with partially folded legs 12. The legs 12 form support portions 14 which are each formed by a respective leg which is closed in an annular configuration in the peripheral direction and which is folded in a zigzag-shaped or meander-shaped configuration.

The stent 10 is formed by a plurality of such support portions 14 which occur in succession in the longitudinal direction. The support portions or leg rings 14 are connected together by way of connecting legs 16. Each two connecting legs which are mutually adjacent in the peripheral direction and the parts, which are in mutually opposite relationship between those connecting legs 16, of the leg rings or support portions 14 define a mesh 18 of the stent 10. Such a mesh 18 represents an opening in the carrier structure or peripheral wall of the stent 10. A corresponding mesh 18 is shown emphasized in FIG. 1.

The number of leg rings or support portions 14 and the length l thereof in relation to the total length L of the stent 10 depends on the purpose of use of the stent. Coronary stents are usually of a shorter overall length L and have a smaller number of support portions 14.

The support portions 14 arranged at the two longitudinal ends of the stent 10 form end portions 20 of the stent. The annularly closed, zigzag-folded legs which form the end closure portions 20 are provided in portion-wise manner with marker elements 22. While the legs 12 and 16 of the stent 10 are preferably made from a nitinol tube as starting material by cutting it out by means of a laser or by spark erosion, the marker elements 22 are subsequently welded to the legs 12.

For that purpose, in the case of the example shown in FIG. 1, in production of the carrier structure by cutting out the legs 12 and 16 from a nitinol tube, corresponding apertures are provided, into which the marker elements 22 are later welded.

As an alternative thereto, it is also possible for the end portions 20 to be produced independently of the rest of the carrier structure of the stent 10 and to be prefabricated, for example completely from a nitinol wire, for example one with a gold core. In that case, the entire end portions 20 respectively form a continuous X-ray marker which, after the operation of cutting out the rest of the carrier structure from a nitinol tube, is connected to the outermost connecting legs 24 by welding. That variant is not specifically shown in FIG. 1 as the only difference in relation to the illustration in FIG. 1 is that the entire end portion 20 forms a continuous marker element 22.

Figure 4:
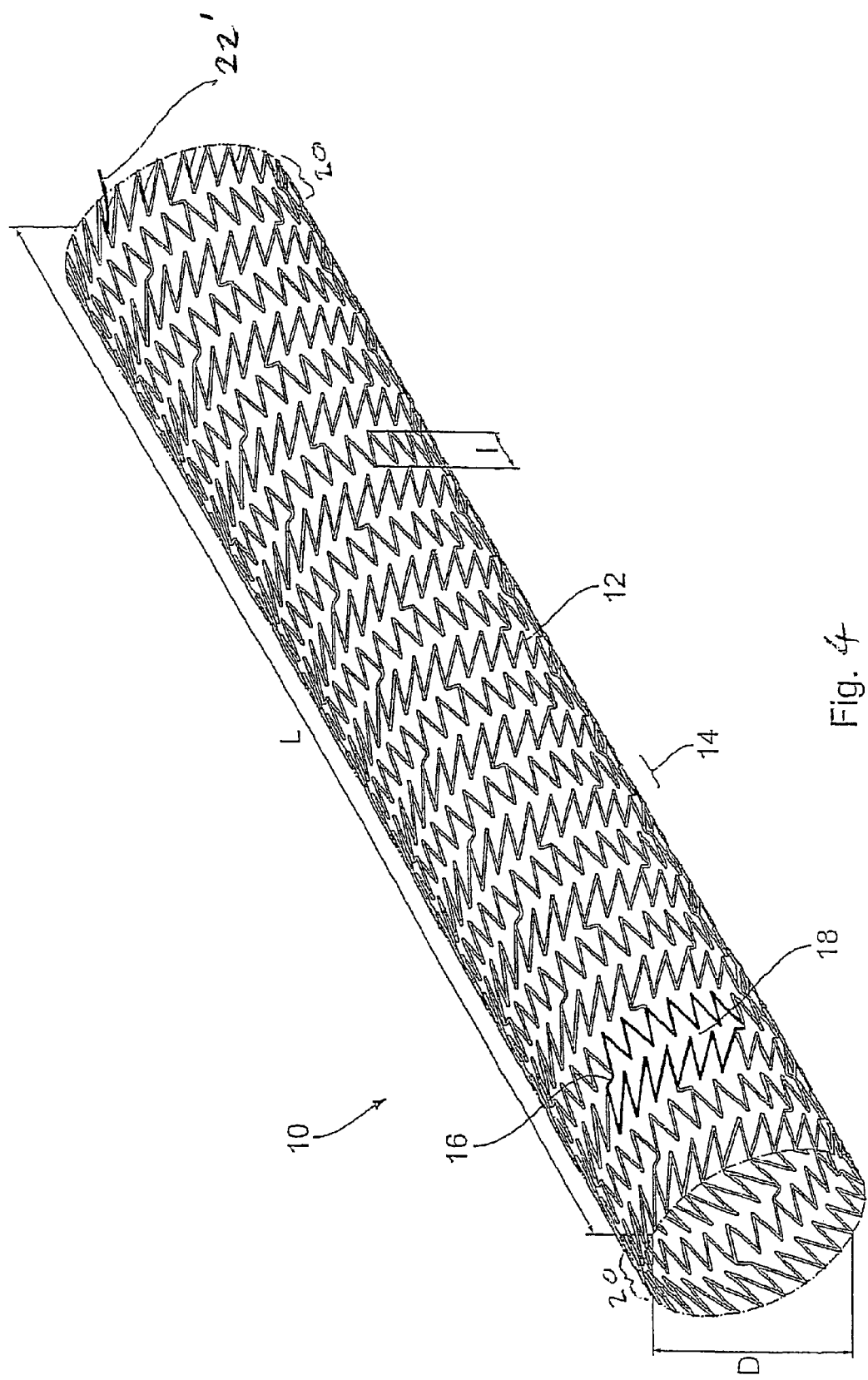
FIG. 4 shows an alternative configuration to FIG. 1.

In a further variant, one or more individual marker elements are welded to the carrier structure of a stent 10, as is shown in FIG. 1. This variant is shown in FIG. 4. Accordingly, the entire carrier structure of the stent including the end portions 20 is cut out of a nitinol tube and only the marker elements 22' are subsequently welded to that carrier structure.

Figure 3:
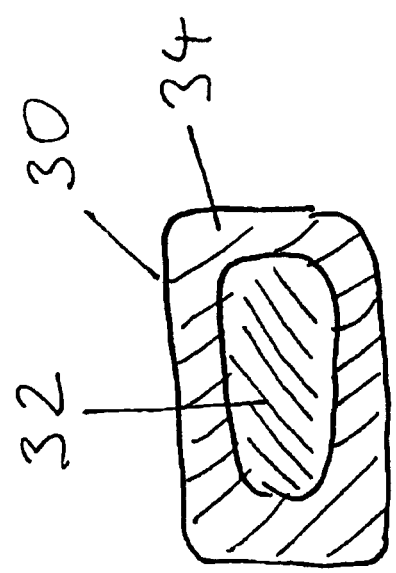
FIG. 3 shows a view in cross-section through a leg portion forming an X-ray marker for stents as shown in FIGS. 1 and 2.

As can be seen from the cross-section through an X-ray marker 22 and 22' respectively in FIG. 3, it is formed by a wire 30 which, in its interior, includes a core 32 of X-ray-opaque material such as for example gold, platinum or palladium. That core 32 is completely enclosed by carrier material 34. In that respect, the carrier material 34 corresponds to the metallic material from which the rest of the stent 10 is produced. A preferred carrier material is nitinol, a titanium nickel alloy, which is also referred to as a shape memory metal. The advantage of such an X-ray marker is that it can be readily joined to the rest of the carrier structure of a stent, for example by welding, without the per se known problems such as transition or contact corrosion occurring. That is of great significance, in particular in the case of self-expanding stents comprising a shape memory metal such as nitinol.

Shape memory metals such as nitinol are preferably used for self-expanding stents. The particularity of such a shape memory metal is that it can assume two shape conditions and it makes a transition from the first shape condition into the second stable shape condition when a change temperature is exceeded. In regard to stents, the first shape condition corresponds to the compressed condition of the stent in which it is introduced for example into a blood vessel or is fitted onto a stent delivery catheter. When the change temperature is reached, the stent has a tendency to assume its expanded condition and develops corresponding expansion forces which have the desired, vessels supporting effect. In that way the stent possibly does not need to be expanded and plastically deformed by means of a balloon. The advantages and preferred design variants of self-expanding stents, in particular of shape memory metals such as nitinol, are basically known to the person skilled in the art. The advantage of a marker element of the kind described herein is that this marker element can basically be combined with all known forms of self-expanding stents, in particular also those of nitinol, without corrosion problems occurring in stents.

We claim:

1. A stent having a metallic, at least partially radiolucent carrier structure comprising a cut out metal tube including legs defining a mesh, and having at least one marker element welded to at least one leg, wherein prior to being welded, the marker element is formed as including a unitary core of a comparatively radiopaque material filling the interior and completely enclosed by a unitary cover layer of a metal or metal compound including material other than the comparatively radiopaque material, and together the comparatively radiopaque material and the unitary cover layer form a core filled wire, wherein the metal or metal compound in the unitary cover layer includes a titanium nickel alloy, and wherein the metal forming the carrier structure is the same titanium nickel alloy included in the unitary cover layer.

2. The stent as set forth in claim 1, wherein the carrier structure is a self-expanding carrier structure.

3. The stent as set forth in claim 2, wherein the carrier structure includes a shape memory metal which changes its shape at a change temperature, wherein the stent is of such a design configuration that the stent retains a compressed condition below the change temperature and assumes an expanded condition above the change temperature.

4. The stent as set forth in claim 1, wherein the unitary cover layer further comprises a silicon carbide (SiC) coating.

5. The stent as set forth in claim 1, wherein the marker element is attached to the carrier structure at the unitary cover layer.

6. The stent as set forth in claim 1, wherein the marker element is attached to the carrier structure in a region of a longitudinal end of the stent.

7. The stent as set forth in claim 1, wherein the comparatively radiopaque material contains gold, platinum and palladium.

8. The stent as set forth in claim 1, wherein the carrier structure includes at least one aperture produced by cutting out at least one of the legs, and wherein the at least one marker element is welded in the at least one aperture.

9. The stent as set forth in claim 1, wherein a plurality of the legs form at least one leg ring.

10. The stent as set forth in claim 9, wherein the at least one leg to which the at least one marker element is welded is a member of the plurality of the legs forming the at least one leg ring.

11. The stent as set forth in claim 9, wherein the at least one marker element forms and end portion.

12. A method of treating a patient, the method comprising implanting a self-expanding stent into the patient, wherein the stent comprises a metallic, at least partially radio translucent carrier structure comprising a cut out metal tube at least partially of titanium-nickel alloy including legs defining a mesh and at least one marker element welded to at least one leg, and wherein the at least one marker element includes a unitary core of a comparatively radiopaque material filling the interior and completely enclosed by a unitary cover layer of a metal or metal compound material other than the radiopaque material, wherein the unitary cover includes the titanium-nickel alloy, and together the comparatively radiopaque material and the unitary cover layer form a core filled wire, and prior to implanting the stent into the patient, forming the stent by cutting the carrier structure out of a tube, forming the at least one marker element with the unitary core and the unitary cover layer, and then welding the at least one marker element to the at least one leg of the carrier structure.

13. The stent of claim 12, further comprising a silicon carbide (SiC) coating.

* * * * *